United States Patent [19]

Mosior

[11] 4,084,594
[45] Apr. 12, 1978

[54] SURGICAL INSTRUMENT AND HANDLE ASSEMBLY THEREFOR

[75] Inventor: Donald J. Mosior, Mundelein, Ill.

[73] Assignee: American Hospital Supply Corporation, Evanston, Ill.

[21] Appl. No.: 730,870

[22] Filed: Oct. 8, 1976

[51] Int. Cl.² .......................................... A61B 17/32
[52] U.S. Cl. ...................................... 128/311; 128/321
[58] Field of Search ............... 128/2 B, 305, 311, 321; 81/177 F; 403/292, 293, 294

[56] References Cited

U.S. PATENT DOCUMENTS

| | | | |
|---|---|---|---|
| 984,756 | 2/1911 | Frisch | 128/321 |
| 2,113,246 | 4/1938 | Wappler | 128/321 |
| 2,790,437 | 4/1957 | Moore | 128/2 B |
| 3,964,468 | 6/1976 | Schulz | 128/321 X |

Primary Examiner—Robert W. Michell
Assistant Examiner—Michael H. Thaler
Attorney, Agent, or Firm—Tilton, Fallon, Lungmus & Chestnut

[57] ABSTRACT

A surgical instrument having miniature cutting and/or grasping elements at its distal end and having a proximal end portion detachably connected to an operating handle assembly. The handle assembly includes a pair of identical spring-loaded interfitting wing lock members which are capable of being cammed outwardly for readily accepting and coupling to the instrument's proximal end and which are constructed for securely retaining the instrument against accidental release. The handles of the assembly are spring-urged into neutral positions to insure proper positioning of such handles for quick coupling of the instrument and handle assembly.

28 Claims, 8 Drawing Figures

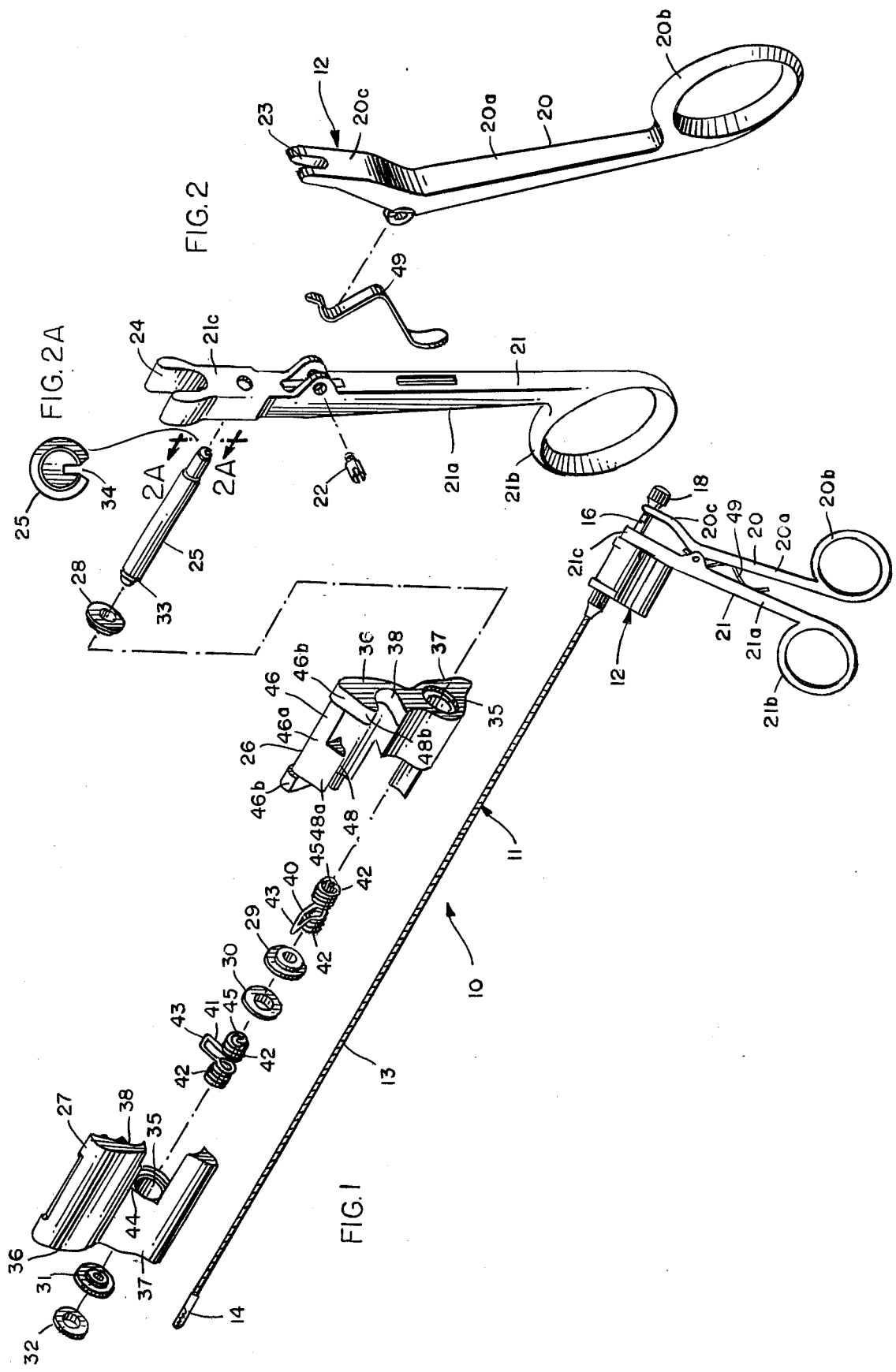

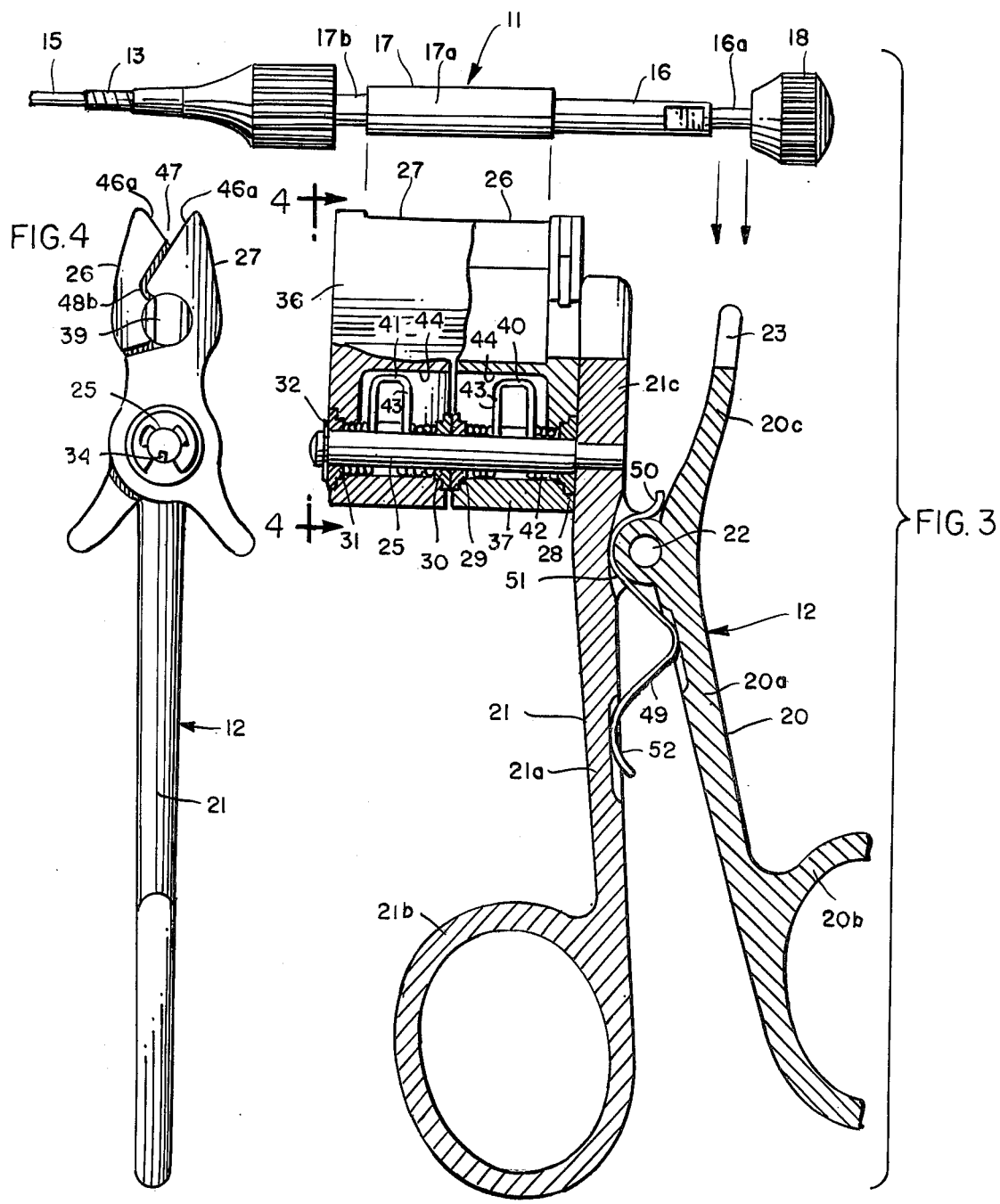

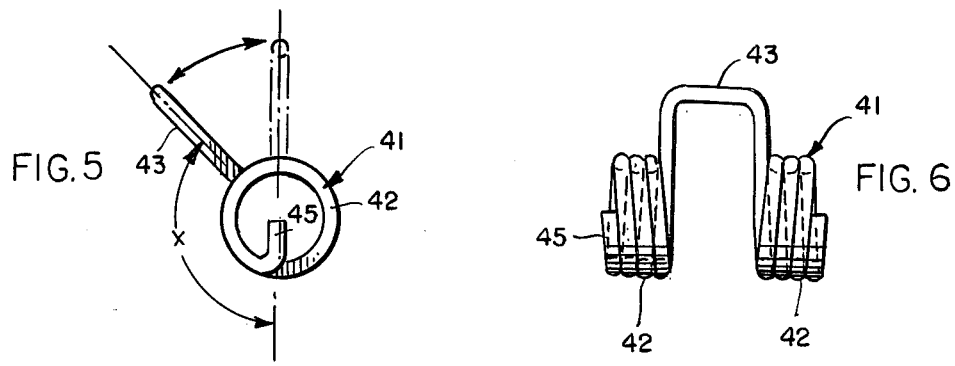
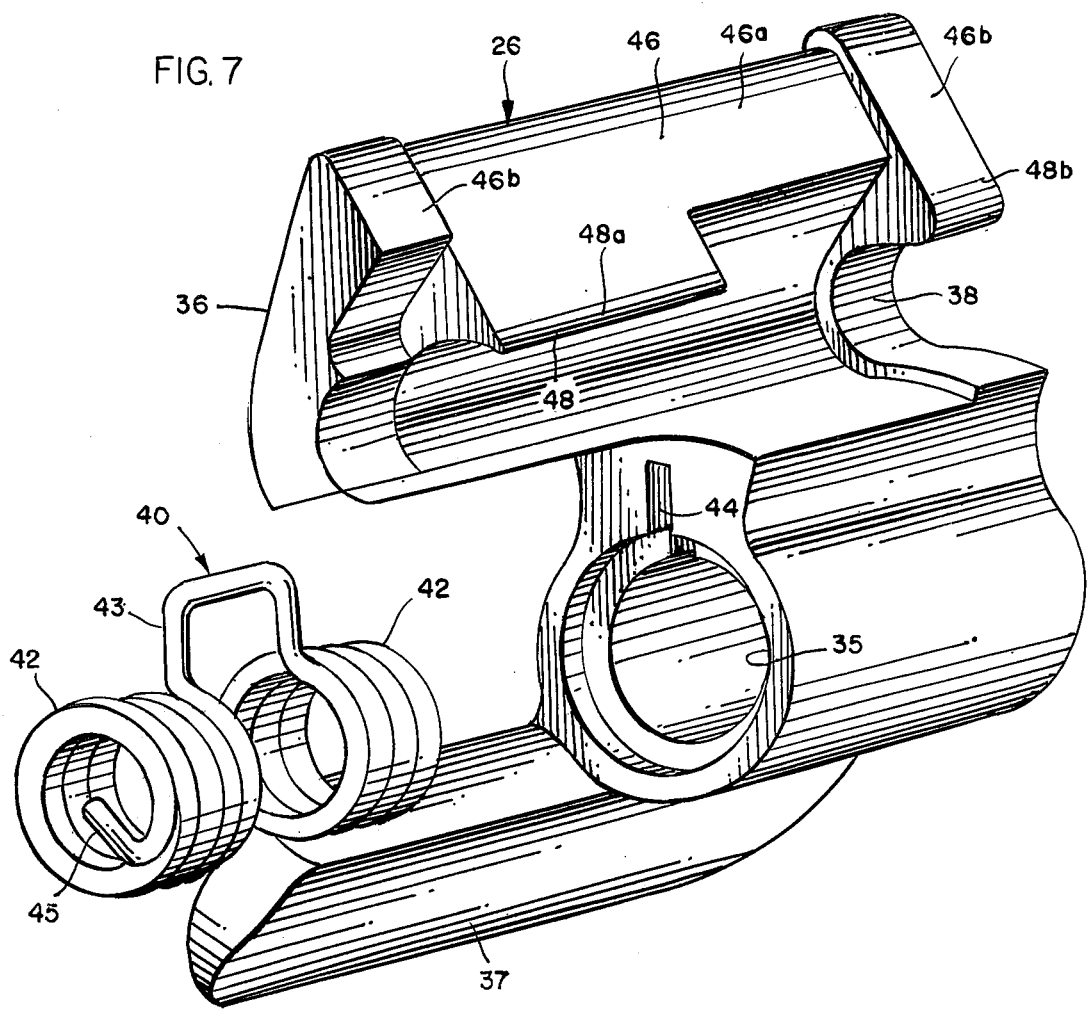

SURGICAL INSTRUMENT AND HANDLE ASSEMBLY THEREFOR

BACKGROUND

One type of microsurgical instrument commonly used in urological procedures, but also generally suitable for use in proctoscopic, bronchoscopic, and other similar procedures, is commonly referred to as a "flexible instrument" and consists of a small-diameter elongated sheath through which an operating rod extends. At the distal end of the instrument are a pair of jaws or elements which may be used for cutting or grasping and which are operatively connected to the rod. The opposite end of the sheath terminates in a tubular housing from which a plunger stem projects, the stem being connected to the rod for operation of the jaws as the stem is moved axially with respect to the housing. Such movement is accomplished by means of an operating handle assembly designed to be attached to the instrument's proximal end.

While a number of manufacturers market flexible instruments having a variety of different cutting or grasping mechanisms, and the handle assemblies for use with such instruments, a notable shortcoming of such constructions lies in the fact that assembly and disassembly of the parts (i.e., instrument and handle units) are usually difficult and time consuming. In some cases the handle assemblies themselves must first be disassembled before flexible instruments may be attached thereto. Depending upon the particular examination or operation involved, a urologist may select any of a variety of different instrument units for coupling to a universal handle unit but, if such coupling requires partial disassembly or special adjustment or manipulation of the handle unit, precious time may be lost. In that regard, it has been observed that the risks of infection in urological procedures are related to the time involved in performing such procedures, the general objective being to complete examination, resection, and other such procedures within a maximum time interval of 70 minutes. Delays encountered because of time devoted to assembling or disassembling instrument and handle units, or because of difficulties in securing replacement units should any parts be dropped during such assembling or disassembling procedures (procedures normally performed by the urologist while in a standing position), may therefore have serious consequences in increasing a patient's risk of infection.

Patent references further illustrative of the art are U.S. Pat. Nos. 2,790,437, 2,113,246, and 3,895,636.

SUMMARY

This invention is concerned with a surgical instrument and a handle assembly which may be easily and quickly connected to each other to form an operative combination. Disassembly may also be readily achieved; however, despite the ease with which such parts may be intentionally detached, there is virtually no possibility of inadvertent separation of the two components.

The instrument takes the form of a sheath, which may be highly flexible or relatively rigid, a housing at the sheath's proximal end and a cutting or clamping mechanism at its distal end, and an operating rod which extends through the sheath, the rod being connected to the mechanism at the distal end and to a plunger at the instrument's proximal end. The handle assembly comprises a pair of handles which are pivotally connected to each other, each handle having a finger-gripping lever or finger-receiving loop disposed below the pivot and a fork portion disposed above the pivot. The fork portions of the two handles have upwardly-facing openings for receiving the proximal end portion of the instrument, such fork portions being movable towards and away from each other as the handles are manipulated to control instrument operation.

One of the handles, which might be referred to as a fixed handle because it is held immovable relative to the surgical instrument when the parts are assembled, has a support shaft projecting outwardly in a direction away from the other (movable) handle. A pair of wing lock members are pivotally mounted upon the shaft, the wing lock members having upper clamping portions which are disposed above the shaft and wing portions which project below the shaft. Preloaded springs urge the wing lock members into normally-closed vertically-extending positions wherein the clamping portions engage each other and the wing portions are spaced apart. By manually squeezing the wing portions, the wing lock members may be pivoted into open positions wherein the clamping portions are swung into spaced relation. The clamping portions of the wing lock members have complementary recesses which together define a bore when the wing lock members are in their closed positions. That bore is dimensioned for detachably receiving and supporting the housing portion of the surgical instrument. To connect the parts, the housing portion of the instrument is simply lowered into engagement with cam surfaces at the upper ends of the wing lock members, thereby forcing the clamping portions of the members apart until the housing is in a fully lowered position and is clamped within the bore. Hook portions of the wing lock members prevent a reverse camming action; in other words, the wing lock members in closed positions cannot be forced open simply by a lifting force exerted on the clamped housing of the instrument.

Manufacture and field repair are greatly facilitated by reason of the fact that the two wing lock members are identical to each other. Each member is urged into its closed position, and is held in that position under preload, by a spring element, the spring elements for the two members being identical. Should repair or replacement of parts become necessary, the wing lock members can be easily removed from the shaft and separated from their spring elements. After repair or the substitution or replacement parts, such parts may be reassembled without concern as to whether a component formerly disposed in a right-hand position might be improperly reassembled in a left-hand position, since such parts are fully interchangable.

The handles may be pivoted to shift their fork portions between fully open and fully closed positions. A positioning spring engages both of the handles to urge them into neutral positions wherein the fork positions are spaced apart a selected distance intermediate the maximum and minimum distances. That selected distance is predetermined to match a dimension at the proximal end of the surgical instrument so that the fork portions of the handles will operatively receive the plunger stem when the housing of the instrument is urged downwardly into seated position between the wing lock members.

Other advantages and objects of the invention will become apparent from the specification and drawings.

DRAWINGS

FIG. 1 is a side elevational view showing a surgical instrument and handle assembly in combined operative form.

FIG. 2 is an exploded perspective view of the components of the handle assembly.

FIG. 2A is an enlarged end elevational view of the support shaft taken along line 2A—2A in FIG. 2.

FIG. 3 is an enlarged vertical sectional view of the handle assembly, the handle assembly being shown in conjunction with the proximal end of a surgical instrument to illustrate the dimensional relationship between the parts.

FIG. 4 is an end elevational view taken along line 4—4 of FIG. 3.

FIGS. 5 and 6 are still further enlarged views of the torsion spring used for urging each wing lock member into its closing position.

FIG. 7 is an even further enlarged perspective view of a wing lock member and the torsion spring used therewith.

DESCRIPTION

Referring to FIG. 1 of the drawings, the numeral 10 generally designates an instrument-handle combination comprising an instrument 11 and a handle assembly 12. The instrument is disclosed more fully in co-pending application Ser. No. 730,869, filed Oct. 8, 1976, so that detailed description will be avoided herein except to the extent that such description is necessary for the purpose of revealing the cooperative relationship of parts.

Instrument 11 belongs to the class of miniaturized surgical instruments which are of such small scale that they may be inserted through the sheath of a cystoscope and/or simultaneously along the passage of an interfitted Albarran bridge, during cystoscopic examination. The instrument includes an elongated sheath 13 which is ordinarily flexible (hence the common name, "flexible instrument") but which may if desired be relatively rigid. A jaw assembly 14, conventionally fashioned for tissue grasping and/or cutting, is secured to the sheath at the distal end of the instrument. An operating rod or wire 15 (FIG. 3) extends through the sheath from the jaw assembly and is connected to a stemlike plunger 16 at the instrument's proximal end. The plunger is slidably received in a tubular shank or housing 17, a spring member (not shown) within the housing normally urging the stem 16 into the extended position illustrated in FIG. 3. Near its end, the stem is provided with a reduced zone 16a of square cross section and, at its extreme end, the stem has a knob 18 threaded thereon. As the knob is urged to the left to retract the plunger stem, the jaws of assembly 14 are opened; when released, the knob tends to return to its original position under the influence of the compression spring within housing 17, the jaws of assembly 14 thereby returning to their normally-closed positions.

It is to be understood that the form and size of the jaws of assembly 14 may vary considerably depending upon the particular use to which the instrument is to be put. For example, the jaws may take the form of scissor blades, clamping jaws, or cutting-holding jaws for taking biopsy specimens. Whether one instrument or another is used may depend largely on the results of an immediately-proceeding preoperation examination. Thus, if it is determined from a cystoscopic examination that an area of obstructing tissue should be cut, the urologist may elect to use a flexible instrument having scissor jaws, the instrument then being operatively connected to a universal handle assembly which is capable of being coupled not only to that style and size of instrument, but, alternatively, to any of the other miniature urological instruments of the group.

The handle assembly 12 is shown most clearly in FIGS. 2–4 and includes a pair of handles 20 and 21 pivotally connected to each other by pin 22. The handles have finger-gripping portions 20a and 21a extending downwardly below the pivot, such portions preferably being provided with finger loops 20b and 21b, respectively. The handle portions are also provided with fork portions 20c and 21c, each fork portion having an upwardly-facing opening 23 and 24, respectively, for receiving the plunger stem 16 of instrument 11. Specifically, opening 24 is dimensioned to receive the main cylindrical portion of the plunger stem 16 whereas opening 23 is dimensioned to receive the stem portion 16a of square cross section. Since the plunger stem 16 and housing 17 are secured against independent relative rotation by suitable locking means (not shown), instrument 11 may be fitted into the openings 23-24 of the handles in any of four positions of rotation, such position being selected to suit the nature of the operative procedure required. For example, if it is desired to have the jaws 14 of the instrument move in a vertical plane (i.e., the same plane as handles 20-21), the instrument may be set in either of two positions allowing for either anterior or posterior movement or opening of the jaws by a simple 180° rotation of the instrument within the handle, whereas if the jaws are to move in a horizontal plane then the instrument may be connected in either of the remaining two positions allowing for left or right lateral jaw opening or movement.

One of the handles (21) is equipped with a fixed support shaft 25 which extends in a generally horizontal direction away from the other of the handles (20). Since the shaft supports the clamping means which holds the surgical instrument in fixed position relative to handle 21, that handle may be regarded as a fixed or stationary handle while the other handle (20) may be considered as the movable handle. The clamping means takes the form of a pair of wing lock members 26 and 27 pivotally mounted upon the shaft 25 and retained by means of shoulder washers 28–31 and split retention ring 32. The shaft is provided near its free or distal end with an annular groove 33 for receiving and retaining the ring 32 and, as shown most clearly in FIGS. 2A and 4, is also provided with a longitudinal groove 34. Each wing lock member is of developed shape and is identical in size and configuration to the other such member. The only difference is that such members are reversely mounted upon shaft 25 so that they interfit as depicted most clearly in FIGS. 3 and 4. Each wing lock member has a bore 35 for receiving the pivot shaft 25, an upper clamping portion 36 extending upwardly from that bore, and a lower wing portion 37 extending outwardly and downwardly below that bore. It will also be noted that each of the clamping portions is provided with an axial recess 38 along its inner face, the complementary recesses of the two interfitting members together forming a bore 39 (FIG. 4) of stepped cylindrical configuration for receiving and retaining the cylindrical housing portion 17 of the instrument 11 when the parts are fully assembled and the wing lock members are in their closed positions.

The wing lock members are normally held in the closed positions depicted in FIGS. 3 and 4 by means of torsion springs 40 and 41. The two springs are also identical except for the way they are reversely mounted upon shaft 25. As shown, each torsion spring has a pair of coil portions 42 and an outwardly projecting intermediate portion 43. The outwardly projecting portion 43 is received in a radial slot 44 in each wing lock member and the entire spring element fits into the bore 35 of that member. Each coil 42 also has a radially inwardly projecting positioning arm portion 45 received in the longitudinal grooves 34 of support shaft 25. The angular distance x (FIG. 5) between portions 43 and 45 when the spring is in an untensioned state is less than 180°, as illustrated in FIGS. 2 and 5. In the illustration given, the angular distance x is approximately 135° but it will be understood that other angular distances less than 180° may be selected depending on the extent of preloading desired. The result in any event is that when each wing lock member and spring is assembled as illustrated, the torsion springs will not only urge the members into their closed positions but will exert a continuous preloading force to hold the members in those positions.

The upper clamping portion 36 of each wing lock member is provided with a sloping cam surface 46 comprising a recessed cam surface portion 46a adjoined by a pair of protruding or elevated sloping cam surface portions 46b. The opposing cam surfaces 46 of the two members together define a stepped V-shaped groove having its apex pointing towards the bore 39 which is adapted to receive the housing 17 at the proximal end portion of the instrument 11. It is believed apparent that if the cylindrical housing 17 of the instrument, with its enlarged portion 17a and reduced portion 17b, is urged downwardly into groove 47 then the clamping portions of the wing lock members will be cammed apart to permit entry of the housing into bore 39, at which time the preloaded wing lock members will return to the closed positions illustrated in FIG. 4 to hold the instrument against movement relative to handle 21. It should also be apparent that the offset nature of cam surface portions 46a and 46b not only provides for simultaneous engagement between cam portions 46a, 46b and corresponding housing surface portions 17b, 17a, respectively, but also ultimately provides the stop means necessary for holding and limiting axial travel of the instrument in relation to the handle 21. Since the diameter of housing portion 17b is slightly greater than that of plunger 16, the protruding cam surface portions 46a at the distal ends of the respective wing lock members are free to engage housing surface portion 17b without objectionable simultaneous engagement between the proximal cam surface portions 46a and plunger 16. Similarly, that portion of the stepped bore 39 which ultimately receives reduced housing portion 17b in clamping relation therewith does so without simultaneous frictional interference between the surfaces at the opposite end of the bore and the surface of plunger 16.

Each of the clamping portions 36 is also provided with hook means 48 having offset hook portions 48a and 48b shown most clearly in FIGS. 7, 4, and 2, the offset hook portions being directly developed from and proportional to the offset cam surface portions 46a and 46b, respectively. The hook portions of one wing lock member extend towards the opposing wing lock member a distance beyond the vertical longitudinal midplane of bore 39 when the wing lock members are closed (FIG. 4). As a result, once the proximal end portion of an instrument is received within bore 39, the interfitting hook portions of the opposing wing members will prevent release of the instrument by mere upward force exerted on that instrument. Inadvertent release of the instrument by a reverse camming action of the jaws is therefore effectively prevented. As a practical matter, such release can be achieved only by exerting an external force to pivot the wing lock members into their open positions. Such external force is applied simply by squeezing the downwardly and outwardly sloping wing portions 37 towards each other, thereby pivoting the clamping portions 36 apart and permitting the instrument to be lifted from the handle assembly.

Referring to FIG. 3, it will be noted that handles 20 and 21 are positioned so that as instrument 11 is lowered the housing 17 will be received between the clamping portions of the wing lock members and the reduced portion 16a of the stem will be received in opening 23 of movable handle 20. Such relationship is important if ease of assembly is to be assured. If instead the movable handle were pivoted from the neutral position shown so that the fork portions 20c and 21c were displaced towards fully closed or fully open positions, then opening 23 would misalign with reduced portion 16a to interfere with proper assembly of the parts. To help position the handles with their fork portions spaced apart the predetermined distance shown, a positioning spring 40 is interposed between the handles, the spring having an arm portion 50 above pivot pin 22 for engaging the inside surface of fork portion 20c of the movable handle, an intermediate portion 51 which extends about the pivot pin, and a lower end portion 52 which engages lower handle portion 21a of stationary handle 21. As shown, the lower portion of the spring also engages the inner surface of movable handle 20. In the condition illustrated, the serpentine leaf spring is in an untensioned state. Movement of the handle 20 to shift loops 20b and 21b towards each other, thereby spreading fork portions 20c and 21c further than shown, will result in a tensioning of the intermediate and lower portions of the spring; hence, when the handle 12 is oriented as shown, the spring, along with gravitational force, act to position the movable handle so that the handle assembly is automatically conditioned for proper coupling to the instrument 11.

Should spring 49 become deformed or broken in use, replacement may be easily accomplished simply by unthreading pivot pin 22 to release the spring and allow the substitution of a replacement (FIG. 2).

In the particular embodiment illustrated, spring 49 is operative to urge movable handle 20 in only one direction — that is, in a direction opposing further spreading of fork portions 20c and 21c. No spring force prevents closing of the fork portions because, upon such closing, the lower end 52 of the spring is free to disengage from handle portion 21a. While such a construction is believed preferable because the spring 49 cannot reduce tactile sensitivity in the manipulation of the instrument 11 to open its jaws 14, it is to be understood that, if desired, the lower portion 52 of the spring may be attached to handle portion 21a (either permanently or removably) so that the spring will also resist closing of the fork portions (or spreading of the loop portions) of the handles from the positions shown in FIG. 3.

While in the foregoing an embodiment of the invention has been disclosed in considerable detail for purposes of illustration, it will be understood by those skilled in the art that many of these details may be varied without departing from the spirit and scope of the invention.

I claim:

1. A handle assembly for use with surgical instruments, comprising a pair of vertically extending handles pivotally connected to each other by pivot means defining a horizontal pivot axis, said handles having finger-gripping portions disposed below the pivot means and fork portions above said pivot means, said fork portions having upwardly-facing openings for receiving the proximal end portion of a surgical instrument and being movable towards and away from each other as said handles are pivoted for controlling instrument operation, one of said handles having a support shaft projecting away from the other of said handles, and a pair of wing lock members pivotally mounted upon said shaft, said wing lock members having upper clamping portions disposed above said shaft and wing portions projecting below said shaft, spring means urging said wing lock members into closed positions wherein said clamping portions engage each other and said wing portions are spaced apart, said members being pivoted into open positions by manually squeezing said wing portions together to pivot said clamping portions into spaced relation, said clamping portions having complementary recesses together defining an instrument-receivable bore adapted to align with said openings of said forks when said wing lock members are in their closed positions.

2. The assembly of claim 1 in which said clamping portions of said wing lock members are provided with opposing camming surfaces together defining a downwardly-tapering groove leading towards said bore when said members are closed, said surfaces being engagable by a surgical instrument for camming said members into open positions when such instrument is urged downwardly into said groove.

3. The assembly of claim 1 in which the clamping portion of each of said wing lock members is provided with a hook portion extending towards the opposing wing lock member a distance beyond the vertical longitudinal midplane of said bore when said members are closed, whereby, an instrument received in said bore is locked by said hook portions against release by upward force exerted on such instrument.

4. The assembly of claim 3 in which said wing lock members are substantially identical to each other.

5. The assembly of claim 1 in which said spring means comprises separate torsion spring elements for each of said wing lock members, each torsion spring element having at least one coil portion extending about said shaft, an outwardly-projecting portion received in a slot in said wing lock member, and an inwardly-projecting portion received in a groove in said shaft.

6. The assembly of claim 5 in which said torsion spring elements are preloaded to hold said wing lock members in closed positions under spring tension.

7. The assembly of claim 5 in which said torsion spring elements for said wing lock members are substantially identical to each.

8. The assembly of claim 1 in which said handles are movable about said pivot to shift said fork portions between open and closed positions, and a positioning spring engagable with said handles to urge the same into neutral positions wherein said fork portions are spaced apart a predetermined distance intermediate the distances of said open and closed positions.

9. The assembly of claim 8 in which said positioning spring comprises a leaf spring disposed between said handles and having portions extending above and below said pivot means.

10. The assembly of claim 9 in which said pivot means comprises a removable threaded pin, said positioning spring being removable from engagement with both of said handles when said threaded pin is removed.

11. A handle assembly for use with surgical instruments comprising a pair of vertically extending handles pivotally connected to each other by pivot means having a horizontally-extending pivot axis, said handles having finger-gripping portions disposed below said pivot means and having upwardly extending portions above said pivot means engagable with such an instrument for operating the same, one of said handles having a support shaft projecting away from the other of said handles, a pair of wing lock members pivotally mounted upon said shaft, said wing lock members having upper clamping portions disposed above said shaft and wing portions projecting below said shaft, spring means urging said wing lock members into closed positions wherein said clamping portions engage each other and said wing portions are spaced apart, said members being pivoted into open positions by manually squeezing said wing portions together to pivot said clamping portions into spaced relation, said clamping portions having complementary recesses together defining a bore for holding such instrument when said wing lock members are in their closed positions.

12. The assembly of claim 11 in which said clamping portions of said wing lock members are provided with opposing camming surfaces together defining a downwardly-tapering groove leading towards said bore when said members are closed, said surfaces being exposed for engagement by a surgical instrument for camming said members into their open positions when such instrument is urged downwardly into said groove.

13. The assembly of claim 11 in which said clamping portions of said wing lock members are provided with interfitting hook portions each extending a distance beyond the vertical longitudinal midplane of said bore when said members are closed.

14. The assembly of claim 13 in which said wing lock members are substantially identical to each other.

15. The assembly of claim 11 in which said spring means comprises a pair of torsion spring elements, one for each of said wing lock members, each torsion spring element having at least one coil portion extending about said shaft, an outwardly-projecting portion received in a slot in said wing lock member, and an inwardly-projecting portion received in a groove in said shaft.

16. The assembly of claim 15 in which said torsion spring elements are preloaded to hold said wing lock members in closed positions under spring tension.

17. The assembly of claim 15 in which said torsion spring elements for said wing lock members are substantially identical to each other.

18. In combination, a surgical instrument having an elongated sheath with distal and proximal ends, a jaw assembly at the sheath's distal end, a housing at the sheath's proximal end, an operating rod extending through said sheath and distally connected to said jaw assembly for operating the same, and a plunger connected to said rod within said housing and having a stem projecting axially from said housing, and a handle assembly engagable with and disengagable from said instrument for operating the same, said handle assembly comprising a pair of vertically extending handles pivotally connected to each other by pivot means having a horizontally-extending pivot axis, said handles having finger-gripping portions disposed below the pivot means and stem-engaging portions projecting above said pivot means, one of said handles having a support shaft projecting away from the other of said handles, and a pair of wing lock members pivotally mounted upon said shaft, said wing lock members having upper clamping portions disposed above said shaft and wing portions projecting below said shaft, said clamping portions having complementary recesses together defining a bore receiving said housing of said instrument, spring means urging said wing lock members into closed positions wherein said housing is clamped within said bore and said wing portions are spaced apart, said wing lock members being pivotal into open positions for releasing said instrument housing by manually squeezing said wing portions together to overcome the force of said spring means.

19. The combination of claim 18 in which said housing and said bore are of stepped cylindrical configuration.

20. The combination of claim 18 in which the clamping portion of each of said wing lock members is provided with at least one hook portion extending towards the opposing wing lock member a distance beyond the vertical longitudinal midplane of said bore when said members are closed, whereby, said instrument housing is locked in said bore by said hook portions against release through upward force exerted on said instrument.

21. The combination of claim 18 in which said wing lock members are substantially identical to each other.

22. The combination of claim 18 in which said clamping portions of said wing lock members are provided with opposing camming surfaces together defining a downwardly-tapering groove leading towards said bore when said members are closed.

23. The combination of claim 18 in which said instrument-engaging portions of said handles are fork shaped having upwardly-facing openings receiving the stem of said instrument, said handles being movable to shift said fork portions between open and closed positions, and a positioning spring engagable with both of said handles for urging the same into neutral positions wherein said fork portions are spaced apart a predetermined distance less than said fully open position and greater than said fully closed position.

24. The combination of claim 23 in which said positioning spring comprises a leaf spring disposed between said handles and having portions disposed above and below said pivot.

25. The combination of claim 23 in which said pivot comprises a removable threaded pin, said positioning spring being removable from engagement with both of said handles when said threaded pin is removed.

26. The combination of claim 18 in which said spring means comprises a pair of torsion spring elements, one of said spring elements for each of said wing lock members, each torsion spring element having at least one coil portion extending about said shaft, an outwardly-projecting portion received in a slot in said wing lock member, and an inwardly-projecting portion secured against movement about the axis of said shaft.

27. The combination of claim 26 in which said torsion spring elements are preloaded for holding said wing lock members in closed positions under spring tension.

28. The combination of claim 26 in which said torsion spring elements are substantially identical to each other.

* * * * *